United States Patent [19]
Livingston et al.

[11] Patent Number: 5,854,065
[45] Date of Patent: Dec. 29, 1998

[54] MICROORGANISM SAMPLING DEVICE

[75] Inventors: Dwight Livingston, Fallston, Md.; Seibert Lowe, Loganville; Frederic J. Marsik, New Freedom, both of Pa.

[73] Assignee: Becton Dickinson and Company, Franklin Lakes, N.J.

[21] Appl. No.: 944,173

[22] Filed: Oct. 6, 1997

[51] Int. Cl.$^6$ .................................................. C12M 3/00
[52] U.S. Cl. .................................. 435/309.4; 435/288.3; 435/305.4; 435/307.1
[58] Field of Search .......................... 422/102; 435/288.3, 435/305.1, 305.3, 305.4, 307.1, 309.1, 309.4

[56] References Cited

U.S. PATENT DOCUMENTS

| | | |
|---|---|---|
| 3,203,870 | 8/1965 | Andelin . |
| 3,729,382 | 4/1973 | Shaffer et al. . |
| 5,021,351 | 6/1991 | Ervin . |
| 5,462,874 | 10/1995 | Wolf et al. ............................. 435/297.5 |
| 5,593,891 | 1/1997 | Banes ..................................... 435/305.1 |

*Primary Examiner*—David Redding
*Attorney, Agent, or Firm*—Bruce S. Weintraub

[57] ABSTRACT

A sampling device useful for determining whether microorganisms are present on a given surface includes a lid member and a base member. The lid member includes a flange that provides visual and tactile indications to a technician of the position of their fingers relative to an edge of the lid member. This increases the ability to avoid accidental or inadvertent contact with a sampling media. The flange is provided with a plurality of lugs that operate to maintain some spacing between the flange and a corresponding base member. This spacing is especially advantageous in situations where air flow is desirable within the sampling device. The base member includes a first cavity for supporting a sampling media and a second cavity. The second cavity includes a plurality of ribs that are contoured to securely fit a lid member partially within the second cavity so that a plurality of sampling devices can be stacked in a convenient and reliable fashion.

14 Claims, 4 Drawing Sheets

5,854,065

MICROORGANISM SAMPLING DEVICE

BACKGROUND OF THE INVENTION

This invention generally relates to a device for holding agar media to sample a selected surface for the presence of microorganisms such as bacteria.

There are many instances where it is necessary or desirable to determine whether microorganisms such as bacteria and fungi are present on a selected surface. A variety of sampling devices have been developed over the years for holding an agar media that can be used for sampling such a surface. One difficulty encountered with existing sampling devices is that the person who is using the device may accidentally or inadvertently touch the agar media. This results in an inaccurate surface sampling since the person's finger may have microorganisms present that would obscure testing results. Although this problem has been recognized, a completely satisfactory solution has not been available to overcome this problem.

Another difficulty associated with conventional sampling devices is that it often becomes difficult to remove a lid from a dish because of a moisture seal lock. The nature of the agar media and the configuration of typical sampling devices creates the possibility for a lid to become moisture locked onto a sampling dish. This is undesirable because removal of the lid then becomes difficult, which introduces a further possibility that the user may inadvertently touch the agar media while handling the sampling device.

Still another challenge presented by conventional sampling devices is the ability to maintain, handle and store a plurality of those devices. In many situations, more than one sampling device would be useful at a given time or location. In such situations, it would be advantageous to be able to readily and compactly store the plurality of sampling devices in a manner that maintains the integrity of the samples and maximizes available space.

This invention addresses the needs and overcomes the drawbacks associated with conventional sampling devices as discussed above.

SUMMARY OF THE INVENTION

In general terms, this invention is a device for use in sampling a surface for the presence of microorganisms. The device has two basic components, a base member and a lid member. The base member includes a media supporting surface that is adapted to support an agar media, for example. A continuous wall surrounds the media supporting surface and projects generally away from that surface in a first direction. A peripheral support surface extends generally outward from the continuous wall so that the continuous wall is located between the peripheral support surface and the media supporting surface. A lip portion extends away from the peripheral support surface in a direction that is generally opposite from the first direction.

The lid member includes a generally planar lid surface, which provides a covering across the entire sampling media when the lid member is appropriately placed on the base member. A continuous sidewall extends away from one side of the lid surface. A flange extends generally outward from an edge on the sidewall. A plurality of lugs are provided on the flange so that when the lid member is placed on the base member, the lugs are supported on the peripheral support surface. Therefore, the flange of the lid member is maintained slightly above the peripheral support surface so that air can circulate into the interior of the sampling device. The lugs further provide the advantage of preventing a moisture lock seal from occurring between the flange on the lid member and the peripheral support surface of the base member.

The base member preferably defines a first and second cavity. The first cavity includes the media supporting surface and maintains the agar media in a desired position. The second cavity is opposite from the first cavity and defined by an underside of the media supporting surface and an interior of the lip portion of the base member. The second cavity includes a plurality of ribs that extend generally inward away from an interior surface on the base member lip portion. These ribs preferably include a surface that conforms to an exterior contour on the lid member. Such an arrangement allows one base member to be placed on top of another lid member so that a plurality of sampling devices designed according to this invention can be easily, conveniently and safely stacked for handling and storage.

The various features and advantages of this invention will become more apparent to those skilled in the art from the following detailed description of the presently preferred embodiment. The drawings that accompany the detailed description can be described as follows.

DETAILED DESCRIPTION OF THE PREFERRED EMBODIMENT

Figure 1:
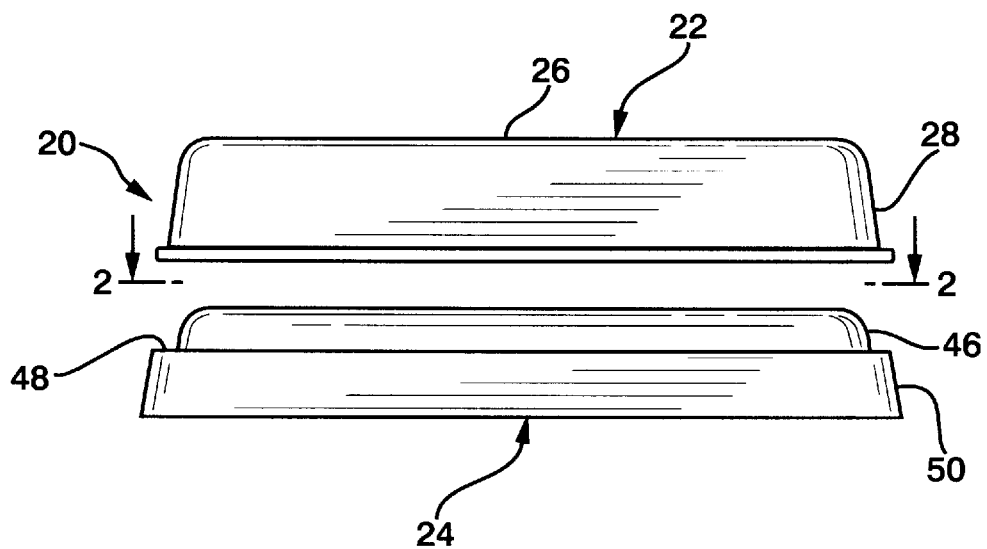
FIG. 1 is a side elevational, exploded view of a sampling device designed according to this invention.

FIG. 1 illustrates a generally circular sampling device 20 designed according to this invention. Sampling device 20 includes a lid member 22 and a base member 24. The lid member 22 includes a generally planar lid surface 26. The term "generally planar" in this specification refers to a flat surface or one that is slightly convex or concave as may be desired. A continuous sidewall 28 extends generally away from the lid surface 26. The exterior diameter at the edge of the lid surface 26 preferably is smaller than an outside diameter at a distal end of the continuous sidewall 28.

The distal end of the sidewall 28 merges into a flange 30 that extends in a generally outward direction. An outer diameter of the flange 30 preferably is greater than the outer diameter of the distal edge of the continuous sidewall 28. The increasing outside diameter of the continuous sidewall 28 and the further increased diameter of the flange 30 provide structure that decreases the likelihood that a user of the device 20 will inadvertently contact the agar media with their fingertips. The flange 30 provides a visual and tactile indication to a user of the position of their fingertips relative to the edge of the lid member 22. This greatly enhances and simplifies a technician's task in making sure that they do not inadvertently touch the agar media of the sampling device.

Figure 4:
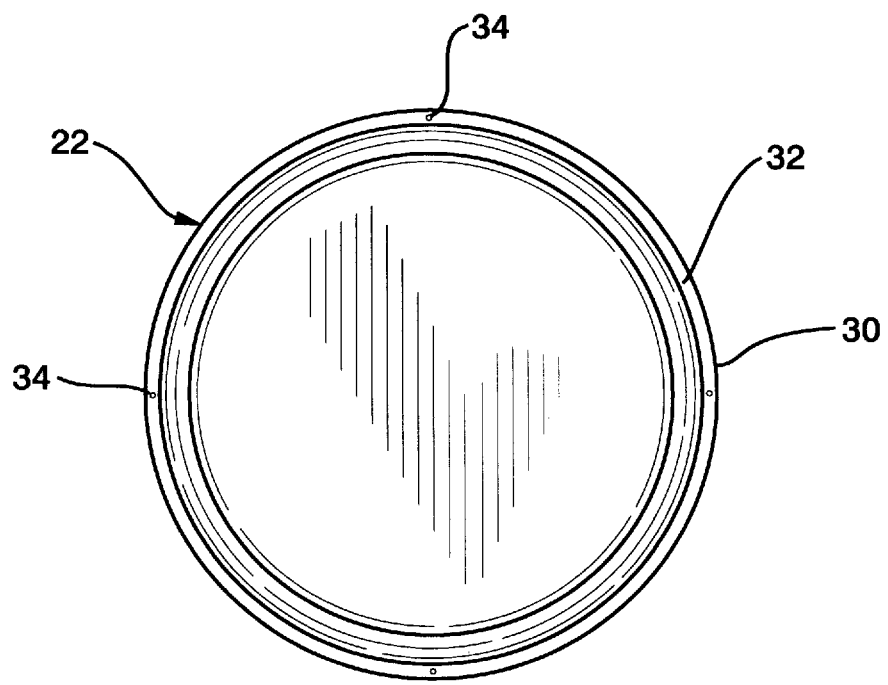
FIG. 4 is a bottom elevational view of the lid member of FIG. 1.
Figure 5:
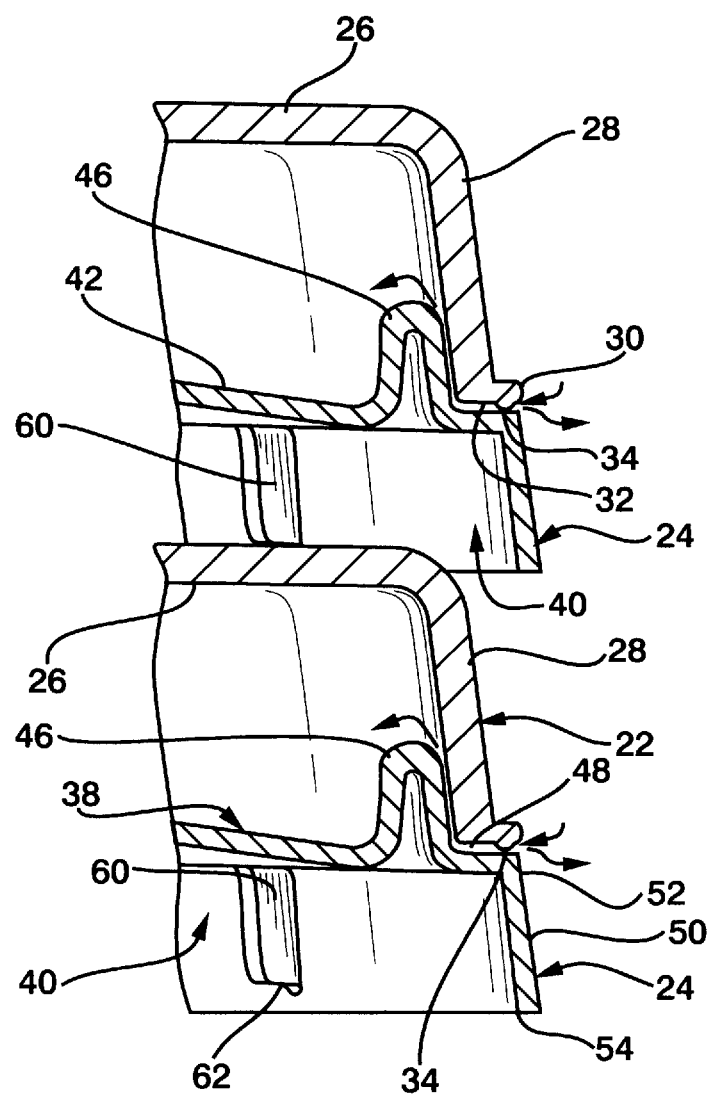
FIG. 5 illustrates two sampling devices in a stacked arrangement.

As best seen in FIGS. 4 and 5, one face 32 on the flange 30, which faces away from the lid surface 26, includes a plurality of lugs 34 that protrude outward and away from the face 32. In the presently preferred embodiment, there are four lugs equally spaced apart around the periphery of the flange 30. The lugs 34 provide structure for maintaining the lid 22 in a preferred relationship with a base member 24 as will become apparent shortly.

Figure 2:
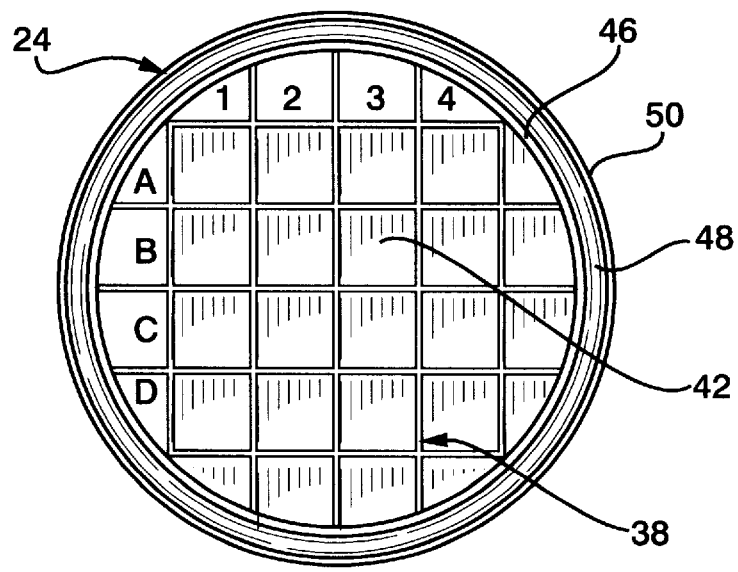
FIG. 2 is a top elevational view taken along the lines 2—2 of FIG. 1.

The base member 24 includes a first cavity 38 and a second cavity 40. The first cavity 38 includes a media supporting surface 42. The media supporting surface 42 is adapted to support a conventional agar media, which is useful for sampling surfaces to determine whether microorganisms are present. In the presently preferred embodiment, a grid system 44 as shown in FIG. 2 facilitates counting microorganisms in a conventional manner.

The outer edge of the first cavity 38 is defined by a continuous wall 46 that surrounds the media supporting surface 42. The wall 46 projects away from the media supporting surface 42 in a first direction (upward according to the drawing). The entire base member 24 preferably is formed from a single piece of plastic such as polystyrene. Therefore, the media supporting surface 42 merges into the continuous wall 46 preferably as illustrated.

A peripheral support surface 48 extends generally outward and away from the continuous wall 46. The peripheral support surface 48 supports the flange 30 of the lid member 22 when the lid member is appropriately placed on the base member 24. More specifically, the lugs 34 rest against the peripheral support surface 48 so that a small gap exists between the face 32 and the peripheral support surface 48. This gap allows for air to flow into and out of the sampling device as may be desired or necessary for many applications. Such air flow is schematically represented by the arrows in FIG. 5. Further, the gap between the face 32 and the peripheral support surface 48 ensures that a moisture lock or seal is not inadvertently created between the lid member 22 and the base member 24.

As best seen in FIG. 5, the length of the lid member sidewall 28 is greater than the height of the base member wall 46. This configuration ensures that the inside of the lid surface 26 will not contact the sampling media when the lid 22 is placed on the base 24.

A lip portion 50 extends away from the peripheral support surface 48 in a second direction, which preferably is generally opposite the first direction mentioned above. The lip portion 50 includes a first edge 52 that is adjacent the peripheral support surface 48 and a distal edge 54. An outside diameter at the first edge 52 preferably is smaller than an outside diameter at the distal edge 54. The increase in diameter along the lip portion 50 provides further structure that enhances the ability of a technician to avoid accidental or improper contact with the sampling media when handling the base member 24.

Figure 3:
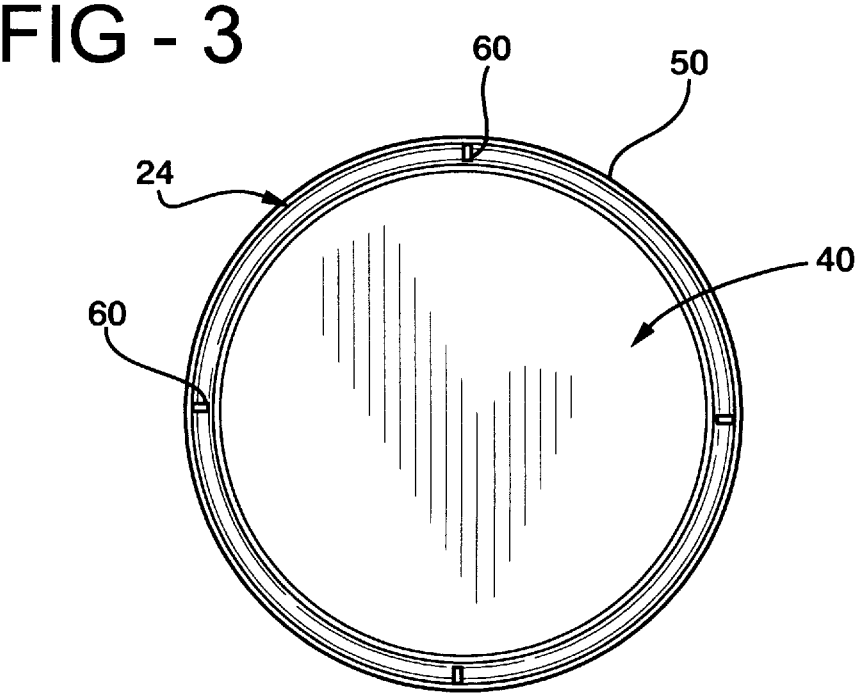
FIG. 3 is a bottom elevational view of the base member of FIGS. 1 and 2.

As best shown in FIGS. 3 and 5, the second cavity 40 is defined by the underside of the media supporting surface 42 and the interior surface of the lip portion 50. A plurality of ribs 60 extend generally inward from the interior surface of the lip portion 50. Each rib 60 includes a surface contour that receives an upper portion of the exterior contour on the lid member 22. Specifically, a rib surface 62 preferably engages the lid surface 26 of the lid member 22. There preferably are four ribs 60 equally spaced apart by 90° within the second cavity 40. The fit between a lid member and ribs on an adjacent base member preferably provides a reliable stacking arrangement that allows easy acess to any selected device 20 within a stack. Ther should be no difficulty in separating a chosen base and lid member from an adjacent base member and, at the same time, there should be minimal radial play between the two members when they are stacked.

The ribs 60 provide a convenient, reliable and economical system for handling, maintaining and storing a plurality of sampling devices 20.

The foregoing description is exemplary rather than limiting in nature. Variations and modifications to the disclosed embodiment may become apparent to those skilled in the art that do not necessarily depart from the purview and spirit of this invention. For example, generally circular sampling devices are illustrated and described, but other configurations may be useful. Accordingly, the legal scope of protection granted to this invention can only be determined by studying the following claims.

What is claimed is:

1. A device for use in sampling a surface for the presence of microorganisms, comprising:
   a base member including
      a media supporting surface that is adapted to support a sampling media,
      a continuous wall surrounding said media supporting surface and projecting generally away from said surface in a first direction,
      a peripheral support surface extending generally outward from said continuous wall such that said continuous wall is between said peripheral support surface and said media supporting surface,
      a lip portion extending away from said peripheral support surface in a second direction that is generally opposite from said first direction; and
   a lid member including
      a generally planar lid surface,
      a continuous sidewall having an inside facing surface and outside facing surface, said sidewall extending away from a first side of said lid surface,
      a flange extending generally outward from said outside facing surface of said sidewall distal from said lid surface, and
      a plurality of lugs protruding from said flange in said second direction such that said lugs bear against said peripheral support surface and said flange is spaced from said peripheral support surface when said lid member is placed on said base member.

2. The device of claim 1, further comprising a plurality of ribs extending generally inward from an interior surface on said lip portion, said ribs each having a contour that conforms to an exterior of said lid surface so that said lid member is received against said ribs in a nesting fashion when said ribs are placed adjacent said lid surface.

3. The device of claim 2, wherein said base member and said lid member are generally circular and said continuous wall, said lip portion, said continuous sidewall and said flange are all generally annular.

4. The device of claim 3, wherein there are four said lugs spaced apart on said flange by 90 degrees.

5. The device of claim 3, wherein said base member lip portion has a first edge adjacent and continuous with said peripheral support surface and a second edge distal from said peripheral support surface and wherein a first diameter at said first edge is smaller than a second diameter at said second edge.

6. The device of claim 1, wherein said base member and said lid member are generally circular and said continuous wall, said lip portion, said continuous sidewall and said flange are all generally annular.

7. The device of claim 6, wherein there are four said lugs spaced apart on said flange by 90 degrees.

8. The device of claim 6, wherein said base member lip portion has a first edge adjacent and continuous with said peripheral support surface and a second edge distal from said peripheral support surface and wherein a first diameter at said first edge is smaller than a second diameter at said second edge.

9. The device of claim 1, wherein said lid sidewall has a first length and said base continuous wall has a second length that is less than said first length.

10. A system for handling and storing a plurality of devices for sampling a surface for the presence of microorganisms, comprising:

a plurality of base members each having a first cavity adapted to contain and support a sampling media, a peripheral support surface surrounding said first cavity and lying generally within a first plane, a lip portion extending away from said peripheral support surface in a direction that is generally perpendicular to said first plane and forming a second cavity opposite to said first cavity, and a plurality or ribs extending inward into said second cavity from an interior surface on said lip portion;

a plurality of lid members each having a lid surface, a continuous sidewall having an inside facing surface and outside facing surface, said sidewall extending away from said lid surface and a flange extending generally outward from said outside facing surface of said sidewall, said flange having a plurality of lugs protruding from one face of said flange;

wherein said lugs bear against said peripheral support surface and said flange face is spaced from said peripheral support surface when one of said lid members is placed on a corresponding one of said base members to cover over said first cavity of said one base member; and wherein said ribs of said one base member bear against said lid surface on another one of said lid members when said another lid member is placed partially within said second cavity.

11. The system of claim 10, wherein said lid members and said base members are generally circular.

12. The system of claim 11, wherein there are four said lugs on each said lid member spaced apart on said flange by 90 degrees.

13. The system of claim 11, wherein said ribs are equally spaced apart by a preselected arcuate distance on each said base member.

14. The system of claim 11, wherein each said base member lip portion has a first edge adjacent and continuous with said peripheral support surface and a second edge distal from said peripheral support surface and wherein a first diameter at said first edge is smaller than a second diameter at said second edge.

* * * * *